United States Patent [19]

Bernacky

[11] 4,378,799
[45] Apr. 5, 1983

[54] APPARATUS FOR VAGINAL HYGIENE

[76] Inventor: Elizabeth C. Bernacky, 1011 Dettling Rd., Woodland Heights, Wilmington, Del. 19805

[21] Appl. No.: 292,217

[22] Filed: Aug. 12, 1981

[51] Int. Cl.³ .............................................. A61M 7/02
[52] U.S. Cl. ...................................... 604/32; 604/34; 604/36
[58] Field of Search ................ 128/226, 248, 251, 227

[56] References Cited

U.S. PATENT DOCUMENTS

| | | | |
|---|---|---|---|
| 779,164 | 1/1905 | Jamison | 128/226 |
| 825,761 | 7/1906 | Salcedo | 128/251 |
| 1,074,368 | 9/1913 | Kutch . | |
| 2,881,760 | 4/1959 | McGiveran et al. | 128/251 |
| 2,955,956 | 4/1959 | Knoch | 128/251 |
| 3,416,529 | 12/1968 | Weisman | 128/232 |
| 4,203,437 | 5/1980 | Mims | 128/229 |

Primary Examiner—John D. Yasko
Attorney, Agent, or Firm—C. S. Krikelis

[57] ABSTRACT

A vaginal hygiene device comprising an annular supporting cushion, fluid injection and fluid collection means, including an adjustable base with the supporting cushion having a hydrophobic outer surface.

6 Claims, 2 Drawing Figures

APPARATUS FOR VAGINAL HYGIENE

FIELD OF THE INVENTION

This invention concerns an apparatus for providing a cleansing and/or therapeutic fluid into the vaginal region of a patient while at the same time substantially confining the fluid to the vaginal area and avoiding contact of other portions of the body with such fluid.

DESCRIPTION OF THE PRIOR ART

When high frequency radiation is given as part of treatment for uterine cancer, an indelible ink mark is placed on the skin of the patient around the treated area. The patient is instructed to douche daily while lying on her back during the duration of the treatments; however, the patient is also instructed to assure that no water or washing fluid contacts her skin within the marked area, as such contact results in blistering of the wetted area, which is painful to the patient.

Prior art devices to alleviate such a problem are exemplified in applications such as U.S. Pat. No. 1,074,368, M. H. Kutch, issued in 1913 which involve the insertion of a shaped, funnel-like device having a tongue-shaped portion into the outer portions of the vagina in an effort to collect fluids and direct them away from the patient's body. Such device is uncomfortable to use and does not provide for the support of the patient's body. Other devices such as described in U.S. Pat. No. 3,416,529, W. W. Weisman, which provide for patient body support do not offer any means by which treating fluid may be delivered within the vagina and removed therefrom without contacting the patient's skin in the vicinity of the vagina.

The instructions usually given to the patients by the hospital staff, which suggest rolling up towels and wrapping them around the patients' thighs and body in an effort to prevent cleansing fluid from reaching the marked skin areas, are totally inadequate as the towels soon become soaked or fall off or both, especially if the patient has no assistance during the treatment. There is need, therefore, for an improved vaginal hygiene apparatus which is comfortable and easy to use by even an unassisted patient which will deliver a fluid to the vagina and remove it therefrom without contacting said patient's skin externally.

SUMMARY OF THE INVENTION

The above objective may be obtained through the use of the present invention which provides a means whereby fluids can be introduced into and withdrawn from the vagina without the same coming in contact with and wetting the person externally.

It is a further objective of this invention to provide an apparatus which will allow the self-administration of a fluid into the vaginal area without external wetting of the patient and which will support the patient's body into the proper position for easy withdrawal and collection of the fluid from the vagina.

The above objectives are obtained through an apparatus comprising in combination:

an annular cushion having a cut-away portion;

a movable base located adjacent said annular cushion and said cut-away portion;

a fluid container mounted on said base, said container having a first shaped orifice; and a movable elongated fluid injection member extending through said shaped orifice having fluid conduit means connected to said fluid injection member and directed through a second opening in said fluid container.

The annular cushion may further comprise an inner core and an outer, fluid repellent skin.

The flexible conduit may be connected to a fluid supply source and such connection may comprise valve means for regulating the fluid flow.

BRIEF DESCRIPTION OF THE DRAWINGS

The invention will be more fully understood from the following description taken in conjunction with the accompanying drawings which form part of this application and in which.

DETAILED DESCRIPTION OF THE INVENTION

Figure 1:
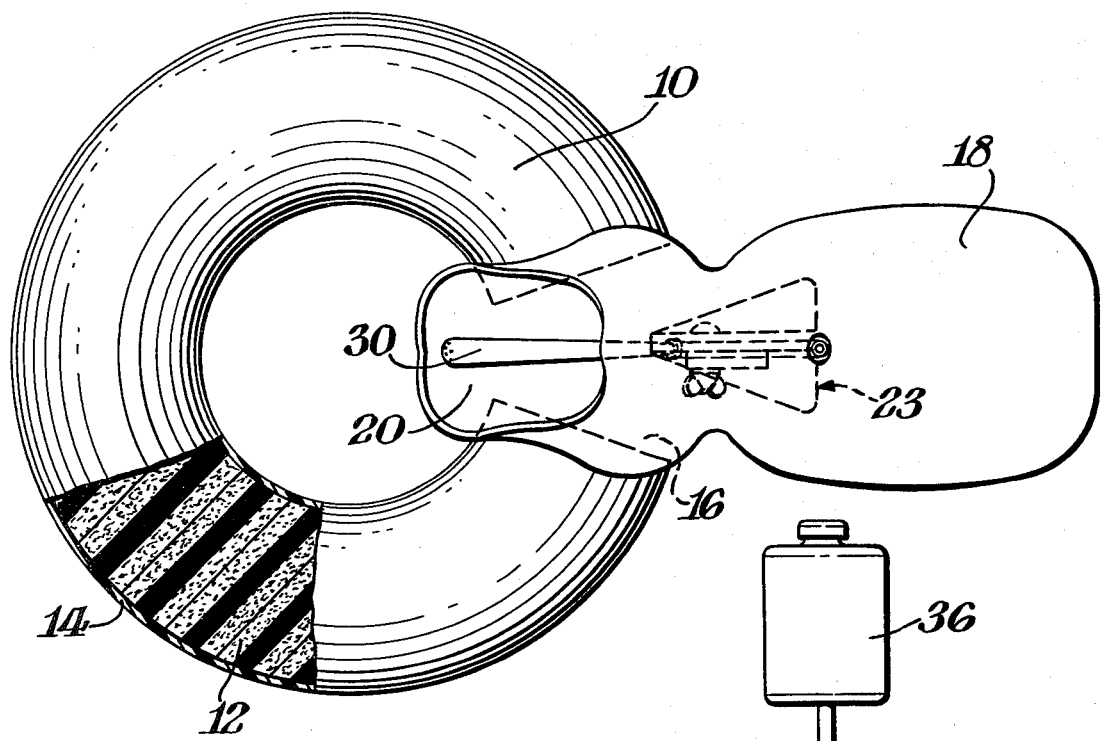
FIG. 1 is a top view of the apparatus for the hygienic treatment of the vagina.
Figure 2:
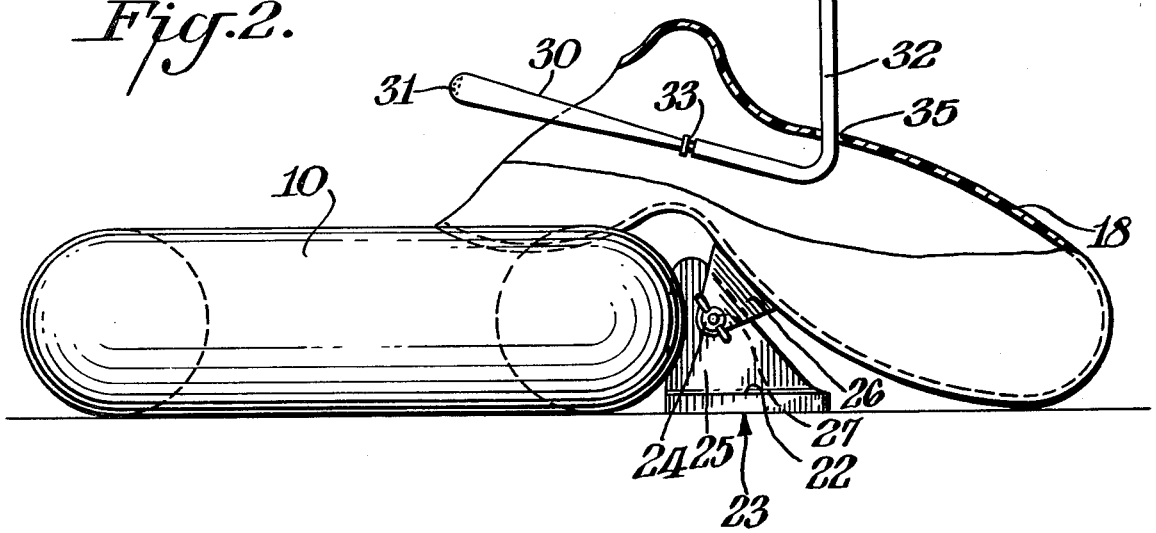
FIG. 2 is an elevation of the same apparatus.

Throughout the following detailed description similar reference numerals refer to similar elements in all figures of the drawings.

With reference to FIG. 1, the present apparatus comprises an annular shaped cushion 10 having a core 12 and an outer skin 14. The core 12 is preferably formed of a somewhat soft or yieldable synthetic material such as polyurethane or similar material to allow the cushion to yield somewhat under the weight of a person lying thereon and provide, in addition to comfort, a seal between the body portion and the cushion in contact therewith. The cushion core 12 is covered by an outer skin 14 which is preferably comprised of a fluid repellent material such as Polyvinylidene chloride, vinylidene chloride copolymer commercially available under the trade name Saran ® by the Saran Lined Pipe Co. The chemical composition of the skin is not important per se, and other materials may be freely substituted provided that such materials are hydrophobic in nature and preferably tend to adhere to the human skin so as to form a watertight seal at the point of contact between the patient's body and the cushion.

The annular cushion does not form a complete ring but is interrupted through a cut-away portion 16 extending the full thickness of the annulus to form an opening connecting the inner hole of the annular cushion with the outside of the cushion. In this cut-away portion there is located a base 22 which may be made of rigid plastic, metal or wood and which comprises a horizontal portion 23 and a vertical portion 25. The horizontal portion 23 is preferably shaped to permit placing the base within the cut-away portion 16 of the cushion without interfering with the sides of the annulus.

At the upper part of the vertical portion 25 there is a hole 27 through which may be fitted a wing-nut and bolt arrangement 24. A fluid container 18 preferably made of some rigid or semirigid plastic material such as polyethylene or polyvinyl chloride or similar material is supported by base 22 through a tab 26 extending from container 18 and fastened to vertical portion 25 by means of a wing-nut and bolt 24. By releasing the pressure provided by the wing-nut the container 18 may be tilted relative to the base and by moving the base in or out relative to the cut-away portion of the cushion, a patient lying on the cushion may bring the mouth portion 20 of the container in intimate and conforming contact with the external region of the vagina, especially so since the container 18 orifice 20 is shaped to a generally elongated, somewhat oval shape which tends to conform to the crotch area of the patient's body.

Through the container opening 20 extends a tubular elongated, preferably rigid fluid injection member 30 terminating to a number of perforations at one end for release of a cleansing stream of fluid. The other end 33 of member 30 is shaped to receive a flexible tubing 32 which is directed through opening 35 at the top of container 18 to a supply of fluid such as container 36. A flow control means, such as valve 34 may be provided to allow selective flow rates. In a simpler embodiment the flow control valve may be replaced with a pressure clamp to stop the fluid flow as desired.

In operation, the assembly of cushion and fluid container with base are placed in a bathtub. The patient places herself on top of the cushion with patient's crotch area located adjacent the cut-away portion of the cushion. The patient then inserts the fluid dispensing member into the vagina and adjusts the position and angle of the fluid container 18 so that the shaped orifice contacts and conforms with the external body portion surrounding the vagina. The patient then opens valve 34 releasing treating or cleansing fluid from container 36 into the vagina at whatever rate is desirable. Excess fluid flows out of the treated body portion and is collected into container 18. Since the cushion skin has formed a seal between the patient's buttocks and the cushion and lifted them above the bathtub floor, even if there is any fluid spillage not collected in container 18, such spillage flows to the bottom of the bathtub without contacting the patient's skin portions in the areas sensitized by the radiation treatment. When the cleansing fluid is of an aqueous nature the hydrophobic external surface of the cushion further assures that no fluid will travel up along the cushion as by soaking and reach the patient's sensitized skin. The full treatment may be performed by the patient unassisted as is readily apparent from the above description.

It will be recognized by the practitioners in the art that the hereinabove described apparatus is also useful in treating other conditions in addition to conditions resulting from the treatment of uterine cancer. The device for instance may be used to facilitate urinary bladder discharge of bedridden patients. Those having benefit of the teachings of this invention as set forth hereinabove may effect modifications thereto. It is possible for instance to replace the cushion having a skin with one without a separate skin but whose outer surface exhibits the same properties as such a skin as described herein. Or the center core may be omitted and an inflatable cushion used instead. However, such modifications are to be construed as lying within the scope of the instant invention.

I claim:

1. A vaginal hygiene apparatus comprising in combination: an annular cushion having a resilient inner core and an outer fluid repellant skin and a cut-away portion;

a movable base adjacent said cushion and said cut-away portion, a fluid container mounted on said base, at an adjustable, predetermined angle, said container having a first, shaped orifice and a movable elongated fluid injection member extending through said shaped orifice having fluid conduit means connected to said fluid injection member and directed through a second opening in said fluid container.

2. The apparatus of claim 1 in which said first shaped orifice has a generally elongated form which conforms to the external body area surrounding the vaginal area.

3. The apparatus of claim 2 in which said base supports said fluid container at an inclined angle.

4. The apparatus of claim 1 in which said outer skin is comprised of hydrophobic material.

5. The apparatus of claim 1 further comprising a source of fluid located outside of the fluid container and connected to the fluid conduit means.

6. The apparatus of claim 5 further comprising fluid flow regulating means connected on line in said fluid conduit means at a port outside of the fluid container and between the fluid container and the source of fluid.

* * * * *